(12) United States Patent
Senn-Bilfinger

(10) Patent No.: US 6,436,953 B1
(45) Date of Patent: Aug. 20, 2002

(54) TETRAHYDROPYRIDOETHERS

(75) Inventor: Jörg Senn-Bilfinger, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/582,212

(22) PCT Filed: Sep. 17, 1999

(86) PCT No.: PCT/EP99/06899

§ 371 (c)(1),
(2), (4) Date: Jul. 19, 2000

(87) PCT Pub. No.: WO00/17200

PCT Pub. Date: Mar. 30, 2000

(30) Foreign Application Priority Data

Sep. 23, 1998 (DE) .......................... 198 43 504

Sep. 23, 1998 (DE) .......................... 98117988

(51) Int. Cl.$^7$ .................. A61K 31/4375; C07D 471/14
(52) U.S. Cl. ........................................ 514/293; 546/82
(58) Field of Search ............................ 514/293; 546/82

(56) References Cited

U.S. PATENT DOCUMENTS 6,197,783 B1 * 3/2001 Senn-Bilfinger ............ 514/293

* cited by examiner

*Primary Examiner*—Alan L. Rotman
(74) *Attorney, Agent, or Firm*—Jacobson Holman, PLLC

(57) ABSTRACT

Compounds of formula (1) in which the substituents have the meanings mentioned in the description, are suitable for the prevention and treatment of gastrointestinal diseases.

13 Claims, No Drawings

TETRAHYDROPYRIDOETHERS

RELATED APPLICATION

This application is directed to subject matter related to that disclosed and claimed in U.S. Pat. No. 6,197,783.

FIELD OF APPLICATION OF THE INVENTION

The invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines having various ring systems fused onto the imidazopyridine parent structure, which are said to be suitable for the treatment of peptic ulcer disorders.

DESCRIPTION OF THE INVENTION

The invention relates to compounds of the formula 1

(I)

in which
R1 is methyl or hydroxymethyl,
one of the substituents R2a and R2b is hydrogen and the other is hydroxy, methoxy, ethoxy, isopropoxy, methoxyethoxy or methoxypropoxy,
one of the substituents R3a and R3b is hydrogen and the other is hydroxy, methoxy, ethoxy, isopropoxy, methoxyethoxy or methoxypropoxy,
where R2a or R2b on the one hand and R3a or R3b on the other hand are not simulataneously hydroxy, and their seats.

Suitable salts of compounds of the formula 1 are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acelic acid, citric acid, D-gluconic acid, benzoic acid, 2-(4-hydroxybenzoyl)benzoic acid, butyric acid, sulfosalicyclic acid, maleic acid, lauric acid, malic acid, fumaric acid, succinic acid, oxalic acid, tartaric acid, embonic acid, stearic acid, toluenesulfonic acid, methanesulfonci acid or 3-hydroxy-2-naphtholc acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula 1 as well as all solvates and in particular all hydrates of the salts of the compounds of formula 1.

The compounds of the formula 1 have three chiral centers. The invention relates to all eight conceivable stereoisomers in any desired mixing ratio with one another, including the pure enantiomers, which are a preferred subject of the invention.

A preferred embodiment of the invention are compounds of the formula 1*

(I*)

in which
R1 is methyl or hydroxymethyl,
one of the substituents R2a and R2b is hydrogen and the other is hydroxy, methoxy, ethoxy, isopropoxy, methoxyethoxy or methoxypropoxy,
one of the substituents R3a and R3b is hydrogen and the other is hydroxy, methoxy, ethoxy, isopropoxy, methoxyethoxy or methoxypropoxy,
where R2a or R2b on the one hand and R3a and R3b on the other hand are not simultaneously hydroxy, and their salts.

An embodiment (embodiment a) of the invention are compounds of the formula 1*,
in which
R1 is methyl,
one of the substituents R2a and R2b is hydrogen and the other is methoxy, ethoxy, isopropoxy, methoxyethoxy or methoxypropoxy,
one of the substituents R3a and R3b is hydrogen and the other is hydroxy, and their salts.

A further embodiment (embodiment b) of the invention are compounds of the formula 1,
in which
R1 is methyl,
one of the substituents R2a and R2b is hydrogen and the other is hydroxy,
one of the substituents R3a and R3b is hydrogen and the other is methoxy, ethoxy, isopropoxy, methoxyethoxy or methoxypropoxy,
and their salts.

A further embodiment (embodiment c) of the invention are compounds of the formula 1*, in which R1 methyl, one of the substituents R2a and R2b is hydrogen and the other is methoxy, ethoxy, isopropoxy, methoxyethoxy or methoxypyropoxy, one of the substituents R3a and R3b is hydrogen and the other is methoxy, ethoxy, isopropoxy, methoxyethoxy or methoxypyropoxy, and their salts.

A further embodiment (embodiment d) of the invention are compounds of the formula 1*, in which R1 is hydroxymethyl, one of the substituents R2a and R2b is hydrogen and the other is methoxy, ethoxy, isopropoxy, methoxyethoxy or methoxypropoxy, one of the substituents R3a and R3b is hydrogen and the other is hydroxy, and their salts.

A further embodiment (embodiment e) of the invention are compounds of the formula 1*, in which R1 is hydroxymethyl, one of the substituents R2a and R2b is hydrogen and the other is hydroxy.

one of the substituents R3a and R3b is hydrogen and the other is methoxy, ethoxy, isopropoxy, methoxyethoxy or methoxypropoxy, and their salts.

A further embodiment (embodiment f) of the invention are compounds of the formula 1*, in which R1 is hydroxymethyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, and their salts.

Preferred compounds of the embodiments a to f are those, in which R3b is hydrogen.

Particularly preferred compounds of the embodiments a to f are those, in which R2a and R3b are hydrogen.

Preferred compounds within the scope of the invention are those of embodiment a, which can be characterized by the formula 1**

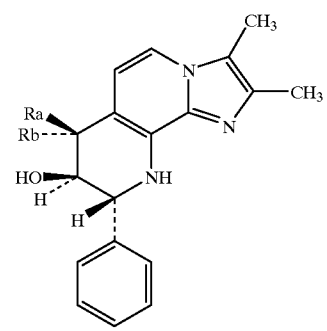

(I**)

in which one of the substituents Ra and Rb is hydrogen and the other is methoxy, ethoxy, isopropoxy, methoxyethoxy or methoxypropoxy and their salts.

Particularly preferred compounds of embodiment a are those of formula 1**, in which Ra is hydrogen and Rb is methoxy, ethoxy, isopropoxy, methoxyethoxy or methoxypropoxy, and their salts.

With the aid of the general formula 1*, the following exemplary preferred compounds according to the invention may actually be mentioned by means of the substituent meanings for R1, R2a, R2b, R3a and R3b in the following Table 1 (Tab. 1):

TABLE 1

| R1 | R2a | R2b | R3a | R3b |
|---|---|---|---|---|
| $CH_3$ | H | $OCH_3$ | OH | H |
| $CH_3$ | H | $OC_2H_5$ | OH | H |
| $CH_3$ | H | $OCH(CH_3)_2$ | OH | H |
| $CH_3$ | H | $OCH_2CH_2OCH_3$ | OH | H |
| $CH_3$ | H | $OCH_2CH_2CH_2OCH_3$ | OH | H |
| $CH_3$ | H | OH | $OCH_3$ | H |
| $CH_3$ | H | OH | $OC_2H_5$ | H |
| $CH_3$ | H | OH | $OCH(CH_3)_2$ | H |
| $CH_3$ | H | OH | $OCH_2CH_2OCH_3$ | H |
| $CH_3$ | H | OH | $OCH_2CH_2CH_2OCH_3$ | H |
| $CH_3$ | H | $OCH_3$ | $OCH_3$ | H |
| $CH_3$ | H | $OC_2H_5$ | $OC_2H_5$ | H |
| $CH_3$ | H | $OCH(CH_3)_2$ | $OCH(CH_3)_2$ | H |
| $CH_3$ | H | $OCH_2CH_2OCH_3$ | $OCH_2CH_2OCH_3$ | H |
| $CH_3$ | H | $OCH_2CH_2CH_2OCH_3$ | $OCH_2CH_2CH_2OCH_3$ | H |
| $CH_2OH$ | H | $OCH_3$ | OH | H |
| $CH_2OH$ | H | $OC_2H_5$ | OH | H |
| $CH_2OH$ | H | $OCH(CH_3)_2$ | OH | H |
| $CH_2OH$ | H | $OCH_2CH_2OCH_3$ | OH | H |
| $CH_2OH$ | H | $OCH_2CH_2CH_2OCH_3$ | OH | H |
| $CH_2OH$ | H | OH | $OCH_3$ | H |
| $CH_2OH$ | H | OH | $OC_2H_5$ | H |
| $CH_2OH$ | H | OH | $OCH(CH_3)_2$ | H |

TABLE 1-continued

| R1 | R2a | R2b | R3a | R3b |
|---|---|---|---|---|
| $CH_2OH$ | H | OH | $OCH_2CH_2OCH_3$ | H |
| $CH_2OH$ | H | OH | $OCH_2CH_2CH_2OCH_3$ | H |
| $CH_2OH$ | H | $OCH_3$ | $OCH_3$ | H |
| $CH_2OH$ | H | $OC_2H_5$ | $OC_2H_5$ | H |
| $CH_2OH$ | H | $OCH(CH_3)_2$ | $OCH(CH_3)_2$ | H |
| $CH_2OH$ | H | $OCH_2CH_2OCH_3$ | $OCH_2CH_2OCH_3$ | H |
| $CH_2OH$ | H | $OCH_2CH_2CH_2OCH_3$ | $OCH_2CH_2CH_2OCH_3$ | H |
| $CH_3$ | $OCH_3$ | H | OH | H |
| $CH_3$ | $OC_2H_5$ | H | OH | H |
| $CH_3$ | $OCH(CH_3)_2$ | H | OH | H |
| $CH_3$ | $OCH_2CH_2CH_3$ | H | OH | H |
| $CH_3$ | $OCH_2CH_2CH_2OCH_3$ | H | OH | H |
| $CH_3$ | OH | H | $OCH_3$ | H |
| $CH_3$ | OH | H | $OC_2H_5$ | H |
| $CH_3$ | OH | H | $OCH(CH_3)_2$ | H |
| $CH_3$ | OH | H | $OCH_2CH_2OCH_3$ | H |
| $CH_3$ | OH | H | $OCH_2CH_2CH_2OCH_3$ | H |
| $CH_3$ | $OCH_3$ | H | $OCH_3$ | H |
| $CH_3$ | $OC_3H_5$ | H | $OC_2H_5$ | H |
| $CH_3$ | $OCH(CH_3)_2$ | H | $OCH(CH_3)_2$ | H |
| $CH_3$ | $OCH_2CH_2OCH_3$ | H | $OCH_2CH_2OCH_3$ | H |
| $CH_3$ | $OCH_2CH_2CH_2OCH_3$ | H | $OCH_2CH_2CH_2OCH_3$ | H |
| $CH_2OH$ | $OCH_3$ | H | OH | H |
| $CH_2OH$ | $OC_2H_5$ | H | OH | H |
| $CH_2OH$ | $OCH(CH_3)_2$ | H | OH | H |
| $CH_2OH$ | $OCH_2CH_2OCH_3$ | H | OH | H |
| $CH_2OH$ | $OCH_2CH_2CH_2OCH_3$ | H | OH | H |
| $CH_2OH$ | OH | H | $OCH_3$ | H |
| $CH_2OH$ | OH | H | $OC_2H_5$ | H |
| $CH_2OH$ | OH | H | $OCH(CH_3)_2$ | H |
| $CH_2OH$ | OH | H | $OCH_2CH_2OCH_3$ | H |
| $CH_2OH$ | OH | H | $OCH_2CH_2CH_2OCH_3$ | H |
| $CH_2OH$ | $OCH_3$ | H | $OCH_3$ | H |
| $CH_2OH$ | $OC_2H_3$ | H | $OC_2H_5$ | H |
| $CH_2OH$ | $OCH(CH_3)_2$ | H | $OCH(CH_3)_2$ | H |
| $CH_2OH$ | $OCH_2CH_2OCH_3$ | H | $OCH_2CH_2OCH_3$ | H |
| $CH_2OH$ | $OCH_2CH_2CH_2OCH_3$ | H | $OCH_2CH_2CH_2OCH_3$ | H |

And the salts of these compounds.

The compounds according to the invention can be prepared as described by way of example in the following examples, or using analogous process steps starting from appropriate starting compounds (see, for example, EP-A-0 299 470 or Kaminski et al., J. Med. Chem. 1985, 28, 876-892). The starting compounds are known or can be prepared analogously to the known compounds. The compounds according to the invention can be prepared for example starting from N-protected 8-amino-imidazo[1,2-a] pyridines according to the following reaction scheme:

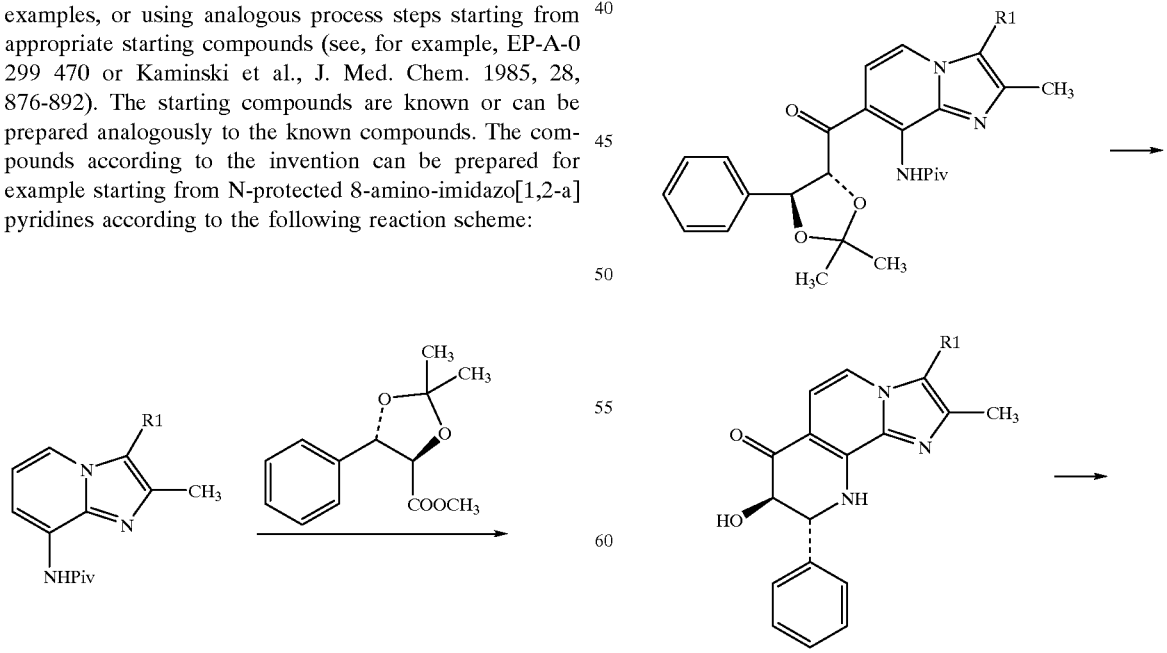

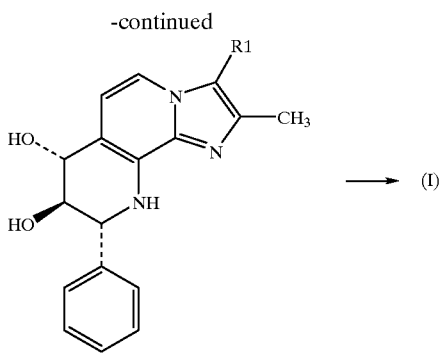

→ (I)

The above scheme represents an example of an enantioselective synthesis. The N-protected (Piv represents a customary protective group, preferably the pivaloyl group), 8-aminoimidazo[1,2-a]pyridine deprotoriated in the 7-position is reacted with an enantiomerically pure dioxolane. This initially leads to a condensation product which can be cyclized under strongly acidic conditions with removal of the protecting groups. The subsequent reduction of the keto group using sodium borohydride leads in over 90% enantiomeric purity to the 7,8-trans-diol indicated. The subsequent etherification which is carried out according to known processes, e.g. as described in the Examples, leads to the final products of formula 1* in which R2a and R3b are hydrogen. The corresponding 7,8-cis-compound is obtained from the mother liquor, which is left after separating off the 7,8-trans-compound, by chromatographic purification.

The substances according to the invention are isolated and purified in a manner known per se, for example, by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as dichloromethane or chloroform, or a low molecular weight aliphatic alcohol (ethanol, isopropanol) which contains the desired acid, or to which the desired acid is subsequently added. The salts are obtained by filtering, reprecipitating, precipitating with a nonsolvent for the addition salt or by evaporating the solvent. Salts obtained can be converted by alkalization or by acidification in the free compounds, which in turn can be converted into salts. In this way, pharmacologically intolerable salts can be converted into pharmacologically tolerable salts.

The pure enantiomers, in particular the pure enantiomers of the formula 1*, to which the invention preferably relates, can be obtained in a manner familiar to the person skilled in the art, for example by enantioselective synthesis (see, for example, the Scheme), by chromatographic separation on chiral separating columns, by derivatization with chiral auxillary reagents, subsequent separation of diastereomers and removal of the chiral auxiliary group, by salt formation with chiral acids, subsequent separation of the salts and liberation of the desired compound from the salt, or by (fractional) crystallization from a suitable solvent. Trans-products obtained (with R2a and R3b=hydrogen) can be converted (at least partly) to the corresponding cis-products (with R2b and R3b =hydrogen) by standing under acidic conditions (e.g. 2 equivalents of acid, such as sulfuric acid) in the corresponding alcohol R2a—OH. Likewise, cis-products obtained can be converted to the corresponding trans-products. The cis- and trans-products are separated e.g. by chromatography or by crystallization.

The following examples serve to illustrate the invention further without restricting it. Likewise, further compounds of the formula 1 whose preparation is not described explicitly can be prepared analogously or in a manner familiar to the person skilled in the art using customary process techniques. The abbreviation min stands for minute(s), h for hour(s) and ee for enantiomeric excess.

EXAMPLES

Final products 1A. (7R, 8R, 9R)-2,3-Dimethyl-8-hydroxy-7-methoxy-9-phenyl-7,8,9,10-tetrahydro-imidazo[1,2-h]-[1,7]nephthyridine Method a 20 g (65 mmol) of (7R, 8R, 9R)-2,3-dimethyl-7,8-dihydroxy-9-phenyl-7,8,9,10-tetrahydro-imidazo[1,2-h][1,7]naphthyridine are dissolved in methanol (350 ml). 13.5 g of sulfuric acid are added and the solution is stirred for 48 h at 50° C. After cooling the reaction mixture is poured into 250 ml of water. The pH is adjusted by aqueous saturated sodium hydrogen carbonate solution to neutral pH. The precipitate is collected and purified on silica gel (eluent: diethylether). 2.5 g of the title compound are obtained as colourless crystals of melting point 164–165° C. (2-propanol).

Method b 10 g (32.5 mmol) of (7R, 8R, 9R)-2,3-dimethyl-7,8-dihydroxy-9-phenyl-7,8,9,10-tetrahydro-imidazo[1,2-h][1.7]naphthyridine are dissolved are dissolved in 200 ml of dry dimethylformamide, 1.9 g of commercially available sodium hydride in parraffin (80%) are added in small portions at room temperature. After 1 h 9.1 g (65 mmol) of methyl iodide, dissolved in 4 ml of dimethylformamide, are added and the mixturer is stirred for an additional hour. The reaction mixture is poured into cold water. 20 ml of a saturated aqueous ammonium chloride solution is added, the yellow precipitate is collected and discarded. The filtrate is extracted several times with ethyl acetate, the combined organic phases are washed several times with water and the solvent is evaporated in vacuo. The solid residue is purified on silica gel (diethylether). 2 g of the title compound are obtained as colourless crystals of melting point 164–165° C. (2-propanol).

1B. (7S, 8S, 9S)-2,3-Dimethyl-8-hydroxy-7-methoxy-9-phenyl-7,8,9,10-tetrahydro-imidazo[1,2-h]-[1,7]naphthyridine The title compound of melting point 161–102° C. is obtained similarly to the procedure described in Example 1, Method a, using (7S,8S,9S)-2,3-Dimethyl-7,8-dihydroxy-9-phenyl-7,8,9,10-tetrahydroimidazo[1,2h][1,7H]naphthyridine as starting material.

2A. (7S, 8R, 9R)-2,3-Dimethyl-8-hydroxy-7-methoxy-9-phenyl-7,8,9,10-tetrahydro-imidazo[1,2-h]-[1,7]naphthyridine 6 g of the title compound are obtained as colourless powder of melting point 108–110° C. after purification on silica gel according to Example 1A, Method a, starting from (7S,8R,9R)-2,3-Dimethyl-7,8-dihydroxy-9-phenyl-7,8,9,10-tetrahydro-imidazo[1,2-h][1,7]naphthyridine.

2B. (7R, 8S, 9S)-2,3-Dimethyl-8-hydroxy-7-methoxy-9-phenyl-7,8,9,10-tetrahydro-imidazo[1,2-h]-[1,7]naphthyridine The title of melting point 171–172° C. is obtained from the mother liquor of Example 1B after purification on silica gel (eluent: diethyl ether).

3. (7R, 8R, 9R)-2,3-Dimethyl-7-ethoxy-8-hydroxy-9-phenyl-7,8,9,10-tetrahydro-imidazo[1,2-h]-[1,7]naphthyridine 500 mg of the title compound are obtained by reaction of (7R, 8R, 9R)-2,3-dimethyl-7,8-dihydroxy-9-phenyl-7,8,9, 10-tetrahydro-imidazo[1,2-h][1,7]naphthyridine with ethanol and sulfuric acid according to Example 1, Method a, after purification on silica gel (eluent: diethylether). Melting point: 188–190° C.

4. (7S, 8R, 9R)-2,3-Dimethyl-7-ethoxy-8-hydroxy-9-phenyl-7,8,9,10-tetrahydro-imidazo[1,2-h]-[1,7]-naphthyridine 800 mg of the title compound of melting point 135–137° C. are obtained as a solid by further purification of the mother liquor of Example 3 on silica gel.

5A. (7R, 8R, 9R)-2,3-Dimethyl-8-hydroxy-7-(2-methoxyethoxy)-9-phenyl-7,8,9,10-tetrahydro-imidazo[1,2-h][1,7]naphthyridine
Method a 5 g of the title compound of melting point 130–1° C. are obtained by reaction of 20 g (7R, 8R, 9R)-2,3-dimethyl-7, 8-dihydroxy-9-phenyl-7,8,9,10-tetrahydro-imidazo[1,2-h][1,7]naphthyridine with 2-methoxy-ethanol according to Example 1, Method a.
Method b To a solution of 100 g of (7R,8R,9R)-2,3-Dimethyl-7,8-dihydroxy-9-phenyl-7,8,9,10-tetrahydroimidazo-[1,2h][1,7] naphthyridine in 1 l of 2-ethoxyethanol, 64 g of concentrated, sulfuric acid are added slowly at room temperature under an argon atmosphere. The rate of addition is such that the temperature of the mixture does not exceed 35° C. After further 15 hours of stirring at room temperature the greenish solution is poured into a mixture of 1 kg of crushed ice and 800 ml of dichloromethane. The pH of the stirred mixture is adjusted to 7.5 by addition of a 10 M aqueous sodium hydroxide solution, the organic layer is separated off, the aqueous layer is extracted three times with dichloromethane (200 ml each), the dichloromethane layers are washed collectively with 500 ml of water (six times) and are then dried over sodium sulfate. After complete evaporation of the solvent under reduced pressure the remaining oily residue is treated with 450 ml of acetone to yield 75 g off-white crystals consisting of a 1:1 mixture of the title compound and its (7S, 8R, 9R)-epimer. The mixture is separated by preparative HPLC using methanol was eluent. 28 g of the title compound of melting point 128°–129° C. are obtained after recrystallization from ethyl acetate.

5B. (7S, 8S, 9S)-2,3-Dimethyl-8-hydroxy-7-(2-methoxyethoxy)-9-phenyl-7,8,9,10-tetrahydro-imidazo[1,2-h][1,7]naphthyridine The title compound of melting point 130°–131° C. is obtained similarly to the procedure described in Example 5A, Method a, using (7S, 8S, 9S)-2,3-Dimethyl-7,8-dihydroxy-9-phenyl-7,8,9,10-tetrahydroimidazo[1,2h][1,7] naphthyridine as starting material.

6A. (7S, 8R, 9R)-2,3-Dimethyl-8-hydroxy-7-(2-methoxyethoxy)-9-phenyl-7,8,9,10-tetrahydro-imidazo[1,2-h][1,7]naphthyridine 7.8 g of the title compound of melting point 131–132° C. are obtained as a solid from the mother liquor of Example 5A after purification on silica gel (eluent: diethyl ether).

6B. (7R, 8S, 9S)-2,3-Dimethyl-8-hydroxy-7-(2-methoxyethoxy)-9-phenyl-7,8,9,10-tetrahydro-imidazo[1,2-h][1,7]naphthyridine The title compound of melting point 131°–132° C. is obtained from the mother liquor of Example 5B after purification on silica gel (eluent: diethyl ether).

7. (7S, 8R, 9R)-2,3-Dimethyl-8-hydroxy-9-phenyl-7-(2-propoxy)-7,8,9,10-tetrahydro-imidazo[1,2-h][1,7]-naphthyridine 1 g of the title compound of melting point 168–9° C. is obtained by reaction of 3 g of 7R, 8R, 9R)-2,3-dimethyl-7, 8-dihydroxy-9-phenyl-7,8,9,10-tetrahydro-imidazo[1,2-h][1,7]naphthyridine with 2-propanol according to Example 1, Method a.

8. (7R,8R,9R)-2,3-Dimethyl-7,8-dimethoxy-9-phenyl-7,8,9, 10-tetrahydro-imidazo[1,2-h][1,7]naphthyridine 8 g of the title compound of melting point 155–156° C. are obtained by reaction of 10 g of (7R,8R,9R)-2,3-dimethyl-7,8-dihydroxy-9-phenyl-7,8,9,10-tetrahydro-imidazo[1,2-h][1,7]naphthyridine with 1,9 g of sodium hydride (80%) and 9,1 g of methyl iodide according to Example 1, Method b.

Starting compounds

A1. 2,3-Dimethyl-7-[(2R,3S)-2,3 O isopropylidene-3-phenylpropan-1-on-1-yl]-8-pivaloylamino-imidazo[1,2-a]pyridine 60 g (0.245 mol) of 2,3-dimethyl-8-pivaloylaminoimidazo[1,2-a]pyridine are dissolved in 1.51 of anhydrous diethyl ether with exclusion of moisture and under an argon atmosphere and cooled to −75° C. By means of a flex needle, 408 ml (0.612 mol) of tert-butyllithium solution (1.5 M in n-pentane) are added dropwise such that the temperature does not exceed −65° C. (30 min). A red suspension is formed. After addition is complete, the suspension is stirred at −75° C. for further 30 min. ⅓ of a solution of 145 g of methyl (2R,3S)-2,3-O-isopropylidene-3-phenylpropionate (ee: 99.05%, Daicel Chiralcel HPLC) in 150 ml of dry THF is then slowly added dropwise at a temperature below −65° C. during the course of 30 min. The residual quantity is then briskly added (5 min), a temperature rise to −60° C. taking place. After addition is complete the cooling bath is removed. On reaching an internal temperature of −30° C., 20 ml of methanol are added and at an internal temperature of 0° C. 200 ml of distilled water are added. The aqueous phase is separated off in a separating funnel, the organic phase is washed five times with 100 ml of distilled water each time, then the organic phase is extracted three times with 10% strength sulfuric acid (200 ml, 50 ml, 50 ml). The sulfuric acid phases are combined, treated with 200 ml of dichloromethane and adjusted to pH 2.3 with 10N sodium hydroxide solution and with ice cooling and vigorous stirring. The organic layer is separated off. The aqueous phase is extracted with 30 ml of dichloromethane. The combined dichloromethane phases are washed twice with a little distilled water. The organic layer is then dried over anhydrous sodium sulfate and the solvent is completely stripped off in vacuo. A brown oil is obtained which is treated with 50 ml of diethyl ether. After seeding, crystals are formed which are filtered off after standing overnight and washed with diethyl ether. After drying in vacuo, 57.7 g (52.5% ee>99%, Daicel Chiralcel HPLC) of the title compound of melting point 76–80° C. are obtained as a pale yellow powder.

A2. 2,3-Dimethyl-7-[(2S,3R)-2,3-O-isopropylidene-3-phenylpropan-1-on-1-yl]-8-pivaloylamino-imidazo[1,2-a]pyridine The title compound (ee: 98.3%, Daicel Chiralcel HPLC) is obtained similarly to the procedure described in example A1 by using methyl (2S, 3R)-2,3-O-isopropylidene-3-phenylpropionate (ee: 98%, Daicel Chiralcel HPLC) as acylating agent.

B1. (8R,9R)-2,3-Dimethyl-8-hydroxy-9-phenyl-7,8,9,10-tetrahydroimidazo[1,2-h][1,7]naphthyridin-7-one 10.8 g (24 mmol) of 2,3-dimethyl-7-[2R,3S)-2,3-O-isopropylidene-3-phenylpropan-1-on-1-yl]-8-pivaloylaminoimidazo[1,2-a]pyridine (ee >95%, Daicel Chiralcel HPLC) are introduced into 50 ml of 70% strength sulfuric acid with ice cooling during the course of 4 min. A suspension is formed in the course of this, which turns into an orange solution after 30 min. After addition is complete, the ice bath is removed and the mixture is stirred on at room temperature. The reaction solution is added after 50 h to ice water and dichloromethane is added, then the mixture is adjusted to pH 8using 6N sodium hydroxide solution and saturated sodium hydrogen-carbonate solution. The organic phase is separated off. The aqueous phase is extracted twice with dichloromethane. The organic phases are combined and washed with a little distilled water. The organic layer is then dried over anhydrous sodium sulfate, filtered and concentrated on a vacuum rotary evaporator. The concentrated residue is chromatographed on silica gel (eluent: dichloromethane/methanol 100/1). The main fraction is concentrated and treated with ethyl acetate, and the title compound crystallizes in the course of this as a yellow solid. This precipitate is filtered off with suction and dried to constant weight in a vacuum drying oven at 50° C. 4.22 g (57%, ee >95%, Daicel Chiralcel HPLC) of the title compound of melting point 231–4° C. are obtained.

B2. (8S,9S)-2,3-Dimethyl-8-hydroxy-9-phenyl-7,8,9,10-tetrahydroimidazo[1,2-h][1,7]naphthyridin-7-one The title compound (ee: 94.0%, Daicel Chiralcel HPLC) is obtained according to the procedure described in example B1 starting from 2,3-dimethyl-7-[(2S,3R)-2,3-O-isopropylidene-3-phenylpropan-1-on-1-yl]-8-pivaloylaminoimidazo[1,2-a]pyridine.

C1. (7R,8R,9R)-2,3-Dimethyl-7,8-dihydroxy-9-phenyl-7,8,9,10-tetrahydroimidazo[1,2h][1,7]-naphthyridine 6 g (19.52 mmol) of (8R,9R)-2,3-dimethyl 8 hydroxy-9-phenyl-7,8,9,10-tetra-hydroimidazo-[1,2-h][1,7]naphthyridin-7-one (see >90% Dalcet Chiralcel HPLC) are suspended in 60 ml of methanol and cooled to −5° to 0° C. in a methanol-ice bath. At this temperature, sodium borohydride (0.81 g, 21.47 mmol) is added by spatula during the course of 0.5 h (evolution of gas). After addition is complete, the mixture is stirred for a further 10 min, and then concentrated in a vacuum rotary evaporator at a bath temperature of 40° C. The oily residue obtained is taken up in distilled water and extracted three times with chloroform. The organic phases are combined and washed with a little water, then dried using anhydrous sodium sulfate and filtered. The filtrate is concentrated on a vacuum rotary evaporator and co-evaporated with acetone; the title compound crystallizes out in the course of this. The precipitate is filtered off, washed with acetone and dried to constant weight at 50° C. in a vacuum drying oven. 5.15 g (85.3%, ee>90%, Daicel Chiralcel HPLC) of the title compound are obtained as a colorless crystallize of melting point 206–9° C.

C2. (7S, 8S, 9S)-2,3-Dimethyl-7,8-dihydroxy-9-phenyl-7,8,9,10-tetrahydroimidazo[1,2h][1,7]-naphthyridine The title compound of mp 207–208° C. (ee: 98.7%, Daicel Chiralcel HPLC) is obtained according to the procedure described in example C1 using (8S,9S)-2,3-dimethyl-8-hydroxy-9-phenyl-7,8,9,10-tetrahydroimidazo[1,2-h][1,7]naphthyridin-7-one as starting material.

D. (7S,8R,9R)-2,3-Dimethyl-7,8-dihydroxy-9-phenyl-7,8,9,10-tetrahydro-imidazo[1,2-h][1,7]naphthyridine 2 g of the mother liquor of Example C1 are chromatographed on silica gel (eluent: ethyl acetate/methanol 19/1) to give 0.35 g of the title compound as an oil which crystallizes upon addition of ethyl acetate. Melting point.: 199–200° C. (ethyl acetate).

Commercial utility

The compounds of the formula 1 and their salts have useful pharmacological properties which make them commercially utilizable. In particular, they exhibit a marked of gastric acid secretion and an excellent gastric acid and intestinal protective action in warm-blooded animals, in particular humans. In this context, the compounds according to the invention are distinguished by a high selectivity of action, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions (such as, for example, stomach ulcers, duodenal ulcers, gastritis, hyperacidic or medicament-related functional gastropathy), which can be caused, for example, by micoorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention furthermore relates to medicaments which contain one or more compounds of the formula 1 and/or their pharmacologically tolerable salts.

The medicaments are prepared by processes known per se, which are familiar to the person skilled in the art. As medicaments, the pharmacologically active compounds according to the invention (=active compounds) are employed either as such, or preferably in combination with suitable pharmaceutical auxiliaries or excipients in the form of tablets, coated tablets, capsules, suppositories, patches (e.g. as TTS), emulsions, suspensions or solutions, where the active compound content is advantageously between 0.1 and 95% and where, by the appropriate choice of the auxillaries and excipients, a pharmaceutical administration form (e.g. a delayed-release form or an enteric form) exactly suited to the active compound and/or to the desired onset of action can be achieved.

The person skilled in the art is familiar, on the basis of his expert knowledge, with auxillaries or excipients which are suitable for the desired pharmaceutical formulations. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in daily dose from approximately 0.01 to approximately 20, preferably 0.05 to 5, in particular 0.1 to 1.5, mg/kg of body weight, if appropriate in the form of several, preferably 1 to 4, individual doses to achieve the desired result. In the case of parenteral treatment, similar or (in particular in the case of intravenous administration of the active compounds), as a rule, lower doses can be used. The optimal dose and manner of administration of the active compounds necessary in each case can easily be determined by any person skilled in the art on the basis of his expert knowledge.

If the components according to the invention and/or their salts are to be employed for the treatment of the abovementioned diseases, the pharmaceutical preparations can also contain one or more pharmacologically active constituents of other pharmaceutical groups. Examples which may be mentioned are: tranquilizers (for example from the benzodiazapines group, e.g. diazepam), spasmolytics (e.g. bietamiverine or camylofin), antiocholinargics (e.g. oxyphencyclimine or phencarbamide), local anesthetics (e.g. tetracaine or procaine), and, if appropriate, also enzymes, vitamins or amino acids.

To be emphasized in this connection, in particular, is the combination of the compounds according to the invention with pharmaceuticals which inhibit acid secretion, such as, for example, H2 blockers (e.g. cimetidine, ranitidine), H+/K+ —ATPase Inhibitors (e.g. omeprazole, pantoprazole), or furthermore with so-called peripheral anticholinergics (e.g. pirenzepine, telenzepine), and with gastrin antagonists with the alm of increasing the main action in an additive or superadditive sense and/or of eliminating or decreasing the side effects, or furthermore the combination with antibacterially active substances (e.g. cephalosporins, tetracyclines, penicillins, macrolides, nitroimidazoles or alternatively bismuth salts) for the control of Helicobacter pylori. Antibacterially active combination components which may be mentioned are, for example, mezlocillin, ampicillin, amoxycillin, cafalothin, cefoxitin, cefofaxime, imipenem, gentamycin, amikacin, arythromycin, ciprofloxacin, metronidazole, clarithromycin, azithromycin and combinations thereof (e.g. clarithromycin+ metronidazole).

Pharmacology

The excellent gastric protective action and the gastric acid secretion-inhibiting action of the compounds according to the invention can be demonstrated in animal experimental models. The compounds according to the invention investigated in the model mentioned below have been provided with numbers which correspond to the numbers of these compounds in the examples.

Testing of the secretion-inhibiting action on the perfused rat stomach

Table A below shows the effects of the compounds according to the invention on the pentagastrin-stimulated acid secretion of the perfused ral stomach in vivo after intravenous administration.

TABLE A

| No. | Dose ($\mu$mol/kg) i.v. | Inhibition of acid secretion (%) |
|---|---|---|
| 1 | 3 | 100 |
| 2 | 3 | 100 |
| 3 | 3 | 100 |
| 4 | 3 | 100 |
| 5 | 3 | 100 |
| 6 | 3 | 100 |
| 7 | 3 | 100 |
| 8 | 3 | 100 |

Methodology

The abdomen of anesthetized rats (CD rat, female, 200–250 g; 1.5 g/kg i.m. urethane) was opened after tracheotomy by means of a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm physiological NaCl solution at 37° C. was continuously passed through the stomach (0.5 ml/min, pH 6.8–6.9; Braun-Unita I). The pH (pH meter 632, glass electrode EA 147; $\phi$=5 mm, Metrohm) and, by tiration with a freshly prepared 0.01 N NaOH solution to pH 7 (Dosimal 665 Metrohm), the secreted HCl were determined in the effluent in each case collected at an interval of 15 minutes.

The gastric secretion was stimulated by continuous infusion of 1$\mu$g/kg (=1.65 ml/h) or i.v. pentagastrin (left femoral vein) about 30 min after the end of the operation (i.e. after determination of 2 preliminary fractions). The substances to be tested were administered intravenously in 1 ml/kg liquid volumes 60 min after the start of the pentagastrin continuous infusion.

The body temperature of the animals was kept at a constant 37.8–38° C. by infrared irradiation and heat pads (automatic, stepless control by means of a rectal temperature sensor).

What is claimed is:
1. A compound of the formula 1

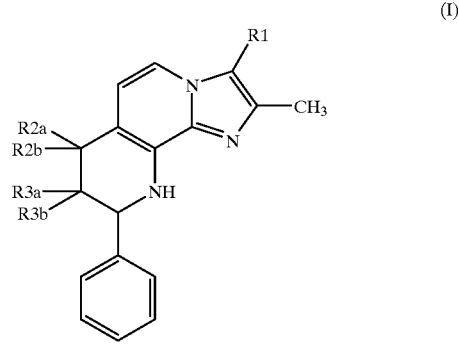

(I)

in which
R1 is methyl or hydroxymethyl,
one of the substituents R2a and R2b is hydrogen and the other is hydroxy, methoxy, ethoxy, isopropoxy, methoxyethoxy or methoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, or a salt thereof.

2. A compound according to claim 1 having the following formula 1*

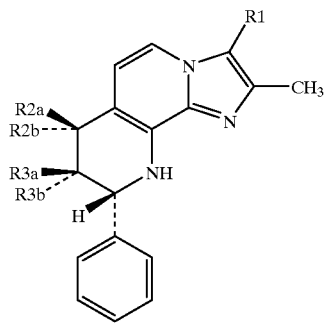

(I*)

in which

R1 is methyl or hydroxymethyl, one of the substituents R2a and R2b is hydrogen and the other is hydroxy, methoxy, ethoxy, isopropoxy, methoxyethoxy or methoxypropoxy, one of the substituents R3a and R3b is hydrogen and the other is hydroxy, methoxy, ethoxy, isopropoxy, methoxyethoxy or methoxypropoxy, where R2a or R2b on the one hand and R3a or R3b on the other hand are not simultaneously hydroxy, or a salt thereof.

3. A compound of formula 1* according to claim 2, in which

R1 is methyl, one of the substituents R2a and R2b is hydrogen and the other is methoxy, ethoxy, isopropoxy, methoxyethyoxy or methoxypropoxy, one of the substituents R3a and R3b is hydrogen and the other is hydroxy, or a salt thereof.

4. A compound of formula 1* according to claim 2 in which

R1 is methyl, one of the substituents R2a and R2b is hydrogen and the other is methoxy, ethoxy, isopropoxy, methoxyethoxy or methoxypropoxy, one of the substituents R3a and R3b is hydrogen and the other is methoxy, ethoxy, isopropoxy, methoxyethoxy or methoxypropoxy, or a salt thereof.

5. A compound of formula 1* according to claim 2, which R3b is hydrogen or a salt thereof.

6. A compound of formula 1* according to claim 2, which R2a and R3b are hydrogen.

7. A compound according to claim 1 having the following formula 1**

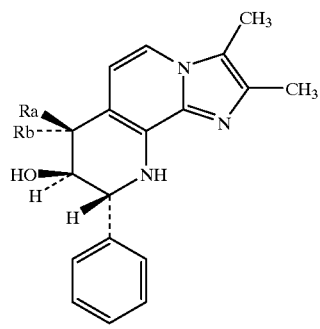

(I**)

in which one of the substituents Ra and Rb is hydrogen and the other is methoxy, ethoxy, isopropoxy, methoxyethoxy or methoxypropoxy or a salt thereof.

8. A compound of formula 1** according to claim 7, in which

Ra is hydrogen and

Rb is methoxy, ethoxy, isopropoxy, methoxyethoxy or methoxypropoxy, or a salt thereof.

9. A compound according to claim 1 which is (7R, 8R, 9R)-2,3-Dimethyl-8-hydroxy-7-(2-methoxyethoxy)-0-phenyl-7,8,9,10-tetrahydro-imidazo[1,2-h][1,7]naphthyridine or a salt thereof.

10. A compound of the formula 1

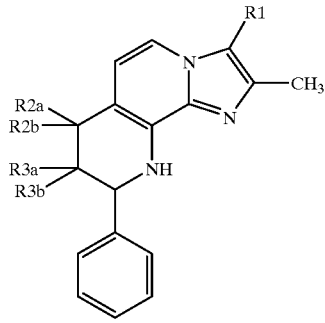

(I)

in which

R1 is methyl or hydroxymethyl, one of the substituents R2a and R2b is hydrogen and the other is hydroxy, methoxy, ethoxy, isopropoxy, methoxyethoxy or methoxypropoxy, one of the substituents R3a and R3b is hydrogen and the other is hydroxy, methoxy, ethoxy, isopropoxy, methoxyethoxy or methoxy propoxy, where R2a or R2b on the one hand and R3or R3b on the other hand are not simultaneously hydroxy or a pharmacologically tolerable salt thereof.

11. A medicament composition comprising a compound as claimed in claim 10 and/or a pharmacologically tolerable salt thereof together a with customary pharmaceutical auxillary and/or excipient.

12. A method for producing a medicament composition by compounding an active ingredient for preventing or treating a gastrointestinal disease, or a pharmacologically-tolerable salt thereof, with a customary pharmaceutical auxiliary and/or excipient, wherein the active ingredient is a compound according to claim 10.

13. A method of treating or preventing an amenable gastrointestinal disease which comprises administering an effective amount of an active ingredient or a pharmacologically tolerable salt thereof to a subject subject to or afflicted with such disease, wherein the active ingredient is a compound according to claim 10.

* * * * *

UNITED STATES PATENT AND TRADEMARK OFFICE
CERTIFICATE OF CORRECTION

PATENT NO.   : 6,436,953 B1
DATED        : August 20, 2002
INVENTOR(S)  : Jörg Senn-Bilfinger It is certified that error appears in the above-identified patent and that said Letters Patent is hereby corrected as shown below:

Column 1,
Line 47, "hydroxy, and their" should read -- hydroxy, --;
Line 48, (starting at the left margin) "seals" should read -- and their salts --;
Line 56, "acelic" should read -- acetic --;
Line 57, "sulfosalicyclic" should read -- sulfosalicylic --.

Column 2,
Line 44, "hydroxy, and" should read -- hydroxy, --;
Line 48, (starting at the left margin) "their salts" should read -- and their salts --;
Line 54, "hydroxy, and their salts." should read -- hydroxy, --;
Line 54, (starting at the left margin) text should read -- and their salts. --;
Line 56, "formula 1" should read -- formula 1* --.

Column 5,
Table 1, the eleventh entry in column 2 under R2a "$OCH_2CH_2CH_3$" should read -- $OCH_2CH_2OCH_3$ --; the nineteenth entry under R2a in the same column "$OC_3H_5$" should read -- $OC_2H_5$ --.

Column 7,
Line 18, "deprotoriated" should read -- deprotonated --;
Line 45, "in" should read -- into --.

Column 8,
Line 12, "nephthyridine" should read -- naphthyridine --;
Line 46, "161" should read -- 101 --.

Column 11,
Line 8, "8using" should read -- 8 using --;
Line 32, "see" should read -- ee --; and "Dalcet" should read -- Daicel --.

Column 12,
Line 1, "marked" should read -- marked inhibition --.

Column 13,
Line 23, "antiocholinargics" should read -- antiocholinergics --;
Line 35, "alm" should read -- aim --;
Line 65, "ral" should read -- rat --.

UNITED STATES PATENT AND TRADEMARK OFFICE
CERTIFICATE OF CORRECTION

PATENT NO. : 6,436,953 B1
DATED : August 20, 2002
INVENTOR(S) : Jörg Senn-Bilfinger It is certified that error appears in the above-identified patent and that said Letters Patent is hereby corrected as shown below:

Column 14,
Line 29, "tiration" should read -- titration ;
Line 30, "Dosimal" should read -- Dosimat --.

Column 15,
Line 62, "which" should read -- in which --;
Line 63, "hydrogen" should read -- hydrogen, --;
Line 65, "hydrogen" should read -- hydrogen, or a salt thereof --.

Column 16,
Line 20, "methoxypropoxy or a salt thereof." should read -- methoxypropoxy --;
Between lines 20 and 21, the text (back to the left margin) should read -- or a salt thereof. --;
Line 28, "-0-" should read -- -9- --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,436,953 B1                                             Page 1 of 1
DATED         : August 20, 2002
INVENTOR(S)   : Jörg Senn-Bilfinger It is certified that error appears in the above-identified patent and that said Letters Patent is hereby corrected as shown below:

Title page,
Item [56], References Cited, U.S. PATENT DOCUMENTS, "6,197,783 B1* 3/2001 Senn-Bilfinger … 514/293" should read
-- 6,197,783 B1* 3/2001 Senn-Bilfinger …. 514/293
   4,468,400 A 8/1984 Gold et al. …. 424/256 --
Insert the following,
       -- FOREIGN PATENT DOCUMENTS
98 42707 A     10/1998        (WO)
95 27714 A                    (WO)
0 299 470      1/1989         (EP)

OTHER PUBLICATIONS
Kaminski et al., Journal of Medicinal Chemistry, Vol. 28, No. 7, 1985, pages 876-92 --

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,436,953 B1 |
| APPLICATION NO. | : 09/582212 |
| DATED | : August 20, 2002 |
| INVENTOR(S) | : Jorg Senn-Bilfinger |

It is certified that error appears in the above-identified patent and that said Letters Patent is hereby corrected as shown below:

Col. 16, Claim 9 should read

--9. A compound according to claim 1 which is (7R, 8R, 9R) -2, 3-dimethyl-8-hydroxy-7- (2-methoxyethoxy) -9-phenyl-7,8,9,10- tetrahydro-imidazo [1,2-h] [1,7] naphthyridine or a salt thereof. --

Signed and Sealed this

Fifth Day of December, 2006

JON W. DUDAS
*Director of the United States Patent and Trademark Office*